United States Patent [19]

Yoder-Short

[11] Patent Number: 5,168,325
[45] Date of Patent: Dec. 1, 1992

[54] INTERFEROMETRIC MEASUREMENT OF GLUCOSE BY REFRACTIVE INDEX DETERMINATION

[75] Inventor: Dale R. Yoder-Short, Dollar Bay, Mich.

[73] Assignee: Board of Control of Michigan Technological University, Houghton, Mich.

[21] Appl. No.: 486,242

[22] Filed: Feb. 28, 1990

[51] Int. Cl.$^5$ .............................................. G01B 9/02
[52] U.S. Cl. ....................................... 356/361; 356/36
[58] Field of Search ................. 356/36, 39, 361, 12 B

[56] References Cited

U.S. PATENT DOCUMENTS

| | | |
|---|---|---|
| 2,434,029 | 1/1948 | Williams . |
| 3,825,347 | 7/1974 | Kaiser . |
| 3,963,019 | 6/1976 | Quandt . |
| 4,169,676 | 10/1979 | Kaiser . |
| 4,690,562 | 9/1987 | Davies et al. ................ 356/361 |
| 4,704,029 | 11/1987 | Van Heuvelen . |

OTHER PUBLICATIONS

Born et al., *Principles of Optics*, Pergamon Press, Oxford, pp. 269-271, 1980.

Primary Examiner—Samuel A. Turner
Attorney, Agent, or Firm—Daniel H. Bliss

[57] ABSTRACT

An apparatus and method for testing the glucose level in a blood sample is provided. The method includes the step of initially filtering a sample of blood to be tested. A beam of light is provided and split into a pair of beams by a beam splitter. The pair of beams travel along generally parallel paths. One path contains a cell of a known optical pathlength and additionally a compensator. The other path has a cell containing the filtered blood sample to be tested. The pair of beams are then recombined by a mirror and a fringe pattern is detected at a detector. From the fringe pattern, the refractive index of the blood sample can be calculated. The refractive index is easily converted to a specific glucose concentration. Alternatively, the original fringe pattern can be restored by changing the effect of the compensator. The refractive index can then be found from the required compensation.

11 Claims, 1 Drawing Sheet

INTERFEROMETRIC MEASUREMENT OF GLUCOSE BY REFRACTIVE INDEX DETERMINATION

BACKGROUND OF THE INVENTION

1. Field of the Invention

The present invention relates generally to a blood glucose monitoring apparatus and method.

2. Description of Related Art

There are approximately between 2 and 4 million people in the United States with diabetes. This amounts to about 2% of the population. Many of these people need to take one or more shots of insulin each day. As a result, there is a need to monitor the glucose level in the blood because these glucose levels often fluctuate due to several factors.

There are many devices on the market known for testing the blood glucose level. One such method is a chemical method using a dye indicator. The glucose in the blood reacts with a reagent and the final color is correlated with a different glucose concentration. This is done by utilizing a small plastic strip and the color is read by visual or photo-reflectance methods.

The accuracy of these tests, however, is relatively low. Their value mainly lies in that they are rapid and simple to use although the accuracy is low.

U.S. Pat. No. 4,704,029 to Van Heuvelen issued Nov. 3, 1987 discloses a blood glucose monitor. The assembly includes a light source which is split into a plurality of beams. One beam is a reference. The other beam is directed toward a prism having a blood sample therebehind to form a reflected beam. The intensity of the reflected beam is compared to the intensity of the reference beam. The angle at which the beam of light is directed at the blood sample is critical. The refractive index of the blood sample is measured by the intensity of the refractor beam. This assembly requires critical angle placement of the prism and blood supply with respect to the incident beam.

SUMMARY OF THE INVENTION

According to the present invention, there is provided an apparatus and a method of measuring the glucose level in a blood sample including measuring the index of refraction of the blood sample by splitting an original beam of light into a first and second beam. The first beam passes through a first cell containing the blood sample while the second beam passes through a second cell of known optical path length and a compensator also of known optical path length. The method finally comprises the steps of recombining the first and second beams to establish a fringe pattern and measuring the fringe pattern.

Accordingly, there is provided a rapid and accurate method to monitor the glucose level in the blood which is sensitive to changes in blood glucose concentration and relies only upon physical measurements thereby eliminating the need for chemical reagents.

Other advantages of the present invention will be readily appreciated as the same becomes better understood by reference to the following description when considered in connection with the accompanying drawings.

DESCRIPTION OF THE PREFERRED EMBODIMENT

Figure 1:
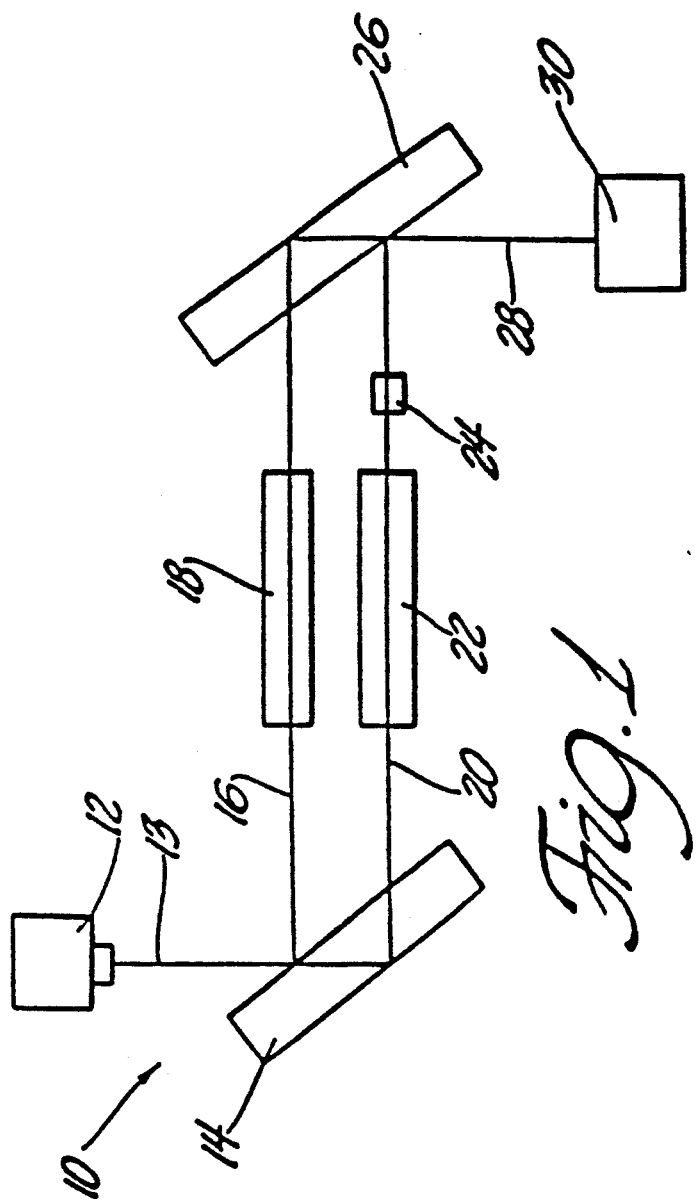
FIG. 1 is a schematic view of an apparatus made in accordance with the present invention.

Referring to FIG. 1, an apparatus for interferometric measurement of glucose made in accordance with the present invention is generally shown at 10. The apparatus 10 includes a light source 12. The light source 12 is preferably a white light source. A monochromatic source may also be used. When using monochromatic light, identical final fringe patterns can exist for a variety of pathlengths. This makes it difficult to differentiate between an increase or a decrease of the optical pathlength (and hence the refractive index) of the material. By utilizing white light, the fringe pattern exists only when the pathlengths are equal.

The light source 12 produces an original beam 13. The beam 13 is directed at a beam splitting mirror 14. The beam splitting mirror 14 splits the beam 13 of light provided by the light source 12 into two separate paths 16 and 20. Any suitable means for splitting the original beam 13 from the light source 12 into the pair of beams 16 and 20 may be used.

The first path, denoted by 16, passes through a first cell 18. The length of the cell is determinable on the sensitivity desired. To calculate the length of the cell, the following refractive index table can be used as a representative of certain glucose levels.

TABLE 1

| Refractive Index of Various Materials | |
|---|---|
| Material | Refractive Index |
| Water | 1.3330 |
| 100 mg sugar/100 ml water | 1.33310 |
| 110 mg sugar/100 ml water | 1.33311 |

For a change in sugar concentration from 100 mg sugar/100 ml water to 110 mg sugar/100 ml water, the refractive index changes by 0.00001. For a change of this magnitude, a value of 100,000 ($10^5$) wavelengths is used to readily detect a change of the fringe pattern at detector 30. For an approximate value of 5000A as the average wavelength of white light, the path length of cell 18 can be calculated from the following equations, where 1.33 is the refractive index of water.

$$\text{path length} = 10^5 = \frac{10^5 \times 5 \times 10^{-7} \text{ m}}{1.33} \simeq 4 \text{ cm}$$

Therefore, approximately a 4 cm pathlength is used to detect a change at detector 30 for a glucose level change of 100 mg to 110 mg in a 100 ml solution. A change in refractive index by one part in $10^5$ will shift the fringe pattern one fringe.

The second beam, denoted by 20, passes through a second cell 22. The length of the second cell 22 is preferably the same as the length of the first cell 18. Further, the second beam 20 passes through a compensator 24. Both the first beam 16 and the second beam 20 are directed onto a combining mirror 26. The combining mirror 26 recombines the pair of light beams 16 and 20 into a single beam 28. Again, any suitable means for recombining the beams 18 and 22 may be utilized within the scope of the present invention. The single final beam 28 is directed or focused upon a detector 30. The detector 30 is generally a photodetector for measuring the intensity of the final beam 28. For a white light source, the intensity will be highest when path lengths 16 and 20 are the same due to constructive interference. As the path lengths differ, due to the difference in refractive indexes of the solutions in cells 18 and 22, the interference at detector 30 will be destructive, thus lessening the intensity virtually to zero.

Initially, apparatus 10 is calibrated by putting a solution of known and identical refractive index into both cells 18 and 22. Since the path lengths are the same, the intensity at detector 30 is the highest. Compensator 24 is set at a reference position. In use, a solution of unknown refractive index is put into cell 18. Since the refractive index is different than the calibration solution in cell 22, the path length is different. Thus, detector 30 receives considerably less illumination. Compensator 24 is then adjusted until the intensity of detector 30 is back to a maximum. From the amount of change in compensator 24, the refractive index of the solution in cell 18 can be determined. This refractive index can then be used to determine the solutions glucose content.

According to the present invention, there is provided a method for testing the level of glucose in the blood stream. In order to test the blood glucose level, a known solution is placed into the first cell 18 and the second cell 22. The light source 12 is then illuminated producing the original beam 13. The beam 13 from the light source is split into a pair of beams 16 and 20 by beam splitting mirror 14. The first beam 16 passes through the first cell 18 containing a known solution and to the combining mirror 26. Simultaneously, the second beam 20 passes through the second cell 22 containing a known solution and through the compensator 24 and is directed to the combining mirror 26. The two beams 16 and 20 are recombined and the final beam 28 is sent to the detector 30. At the detector 30, a fringe pattern is established.

A sample of blood is then filtered to remove all components exceeding a predetermined weight. Particularly, cells and proteins having a molecular weight exceeding one thousand daltons are filtered out of the blood sample. This blood sample is then introduced into the first cell 18. When the filtered blood fills the cell 18, the recombined beam 30 will show a shift in the fringe pattern at the detector 30. The refractive index can be measured either from the shift in the fringe pattern when the sample is changed from the known solution to the unknown solution or from the compensation required at the compensator 24 to restore the original fringe pattern after the unknown solution or blood has been introduced. The compensation is achieved by changing the optical path length of the compensator 24 by a known or predetermined amount.

The assumption is that the major change in the refractive index for the serum, the filtered blood sample, is due to a change in glucose concentration. If, however, the concentration of the electrolytes and simple organic compounds varies so as to appreciably change the refractive index of the blood sample, then the appropriate quantities must be measured and properly accounted or compensated for. Many well known probes exist which could measure the electrolyte concentration for this purpose. Although it is not as easy to separate organic compounds, selective filters may be employed for this purpose or light absorption of these organic compounds can be measured and properly compensated.

Figure 2:
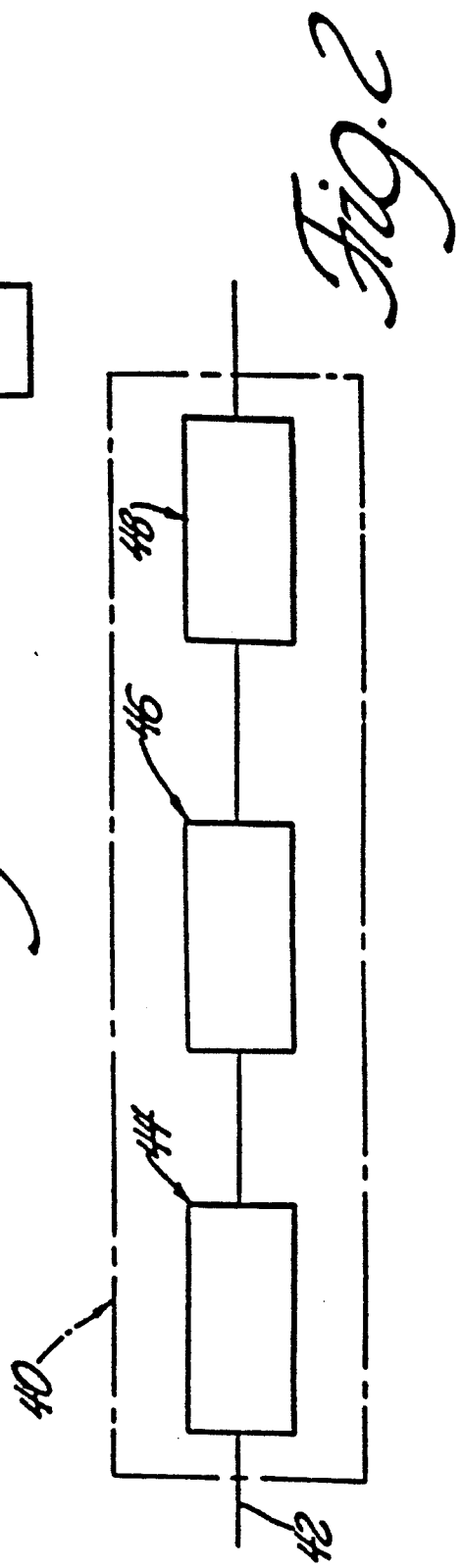
FIG. 2 is a block diagram showing an artifical pancreas utilizing the present invention.

Thus, the present invention has the advantage of providing a portable and accurate apparatus for rapidly and accurately measuring the glucose level from a small sample of blood. Further, the apparatus may be adapted to become a component of an implantable artificial pancreas generally shown at 40 in the block diagram of FIG. 2. This can be accomplished because no chemicals need to be replenished or eliminated for monitoring the blood glucose level. The apparatus or interferometer would be one component of an artificial pancreas. If utilized in such a manner, the blood stream 42 could continuously flow into the interferometer portion generally indicated at 44 of the artificial pancreas 40. It is noted that the interferometer portion 44 of the artificial pancreas 40 is as previously described and shown schematically in FIG. 1. The blood stream 42 flows directly into the first cell of the apparatus. The blood glucose level could be continuously monitored and the information sent to a probe controller generally indicated at 46 which would in turn determine the required insulin output and send the information to the insulin pump generally indicated at 48. The insulin pump 48 injects the correct amount of insulin into the blood stream 42. With such a continuous feedback mechanism, the blood glucose concentration could be regulated much better than by present methods.

The present invention has been described in an illustrative manner. It is to be understood that the terminology which has been used is intended to be a nature of words of description rather than of limitation.

Many modifications and variations of the present invention are possible in light of the above teachings. Therefore, within the scope of the appended claims, the present invention may be practiced otherwise than as specifically described.

What is claimed is:

1. A method of measuring the glucose level in a blood sample comprising the steps of:

placing a known solution into a first cell and second cell;

providing a light source for generating an original beam of light;

splitting the original beam of light into a first and second beam;

passing the first beam through the first cell while simultaneously passing the second beam through the second cell;

recombining the first and second beams into a final beam to establish a fringe pattern;

filtering a blood sample to remove all components exceeding a predetermined weight and placing the filtered blood sample into the first cell;

measuring a shift in the fringe pattern to determine the refractive index of the filtered blood sample.

2. A method as set forth in claim 1 including the step of utilizing a white light source for providing the original beam.

3. A method of measuring the glucose level in a blood sample comprising the steps of:

placing a known solution into a first cell and a second cell;

providing a light source for generating an original beam of light;

splitting the original beam of light into a first and second beam;

passing the first beam through the first cell while simultaneously passing the second beam through the second cell;
recombining the first and second beam into a final beam to establish a fringe pattern;
filtering a blood sample to remove all components exceeding a predetermined weight;
placing the filtered blood sample into the first cell;
measuring a refractive index of the filtered blood sample based on the fringe pattern; and
calculating the glucose level in the filtered blood sample based on the measured refractive index.

4. A method of measuring the glucose level in a blood sample comprising the steps of:
placing a known solution into a first and second cell;
providing a light source for generating an original beam of light;
splitting the original beam of light into a first and second beam;
passing the first beam through the first cell while simultaneously passing the second beam through the second cell;
passing the second beam of light through a compensator;
recombining the first and second beams into a final beam to establish a fringe pattern;
filtering a blood sample to remove all components exceeding a predetermined weight;
placing the filtered blood sample into the first cell; and
measuring the refractive index of the filtered blood sample based on the fringe pattern.

5. A method of measuring the glucose level in a blood sample comprising the steps of:
placing a known solution into a first and second cell;
providing a light source for generating an original beam of light;
splitting the original beam of light into a first and second beam;
passing the first beam through the first cell while simultaneously passing the second beam through the second cell and a compensator;
recombining the first and second beams into a final beam to establish an original fringe pattern;
filtering a blood sample to remove all components exceeding a predetermined weight;
placing the filtered blood sample in the first cell;
calculating the glucose level in the filtered blood sample by adjusting the compensator to restore the original fringe pattern.

6. A method of measuring the glucose level in a blood sample comprising the steps of:
placing a known solution into a first and second cell;
providing a light source for generating an original beam of light;
splitting the original beam of light into a first and second beam;
passing the first beam through the first cell while simultaneously passing the second beam through the second cell;
recombining the first and second beams into a final beam to establish a fringe pattern;
filtering the blood sample to remove all components having a molecular weight exceeding one thousand daltons;
placing the filtered blood sample into the first cell; and
measuring the refractive index of the filtered blood sample based on the fringe pattern.

7. A method of measuring the glucose level of blood comprising the steps of:
filtering a sample of blood to remove cells and proteins exceeding a predetermined weight;
providing a light source for generating an original beam;
splitting the original beam into first and second beams;
placing a first cell containing the filtered blood sample into the first beam of light;
placing a second cell in the second beam;
recombining the beams of light after each has passed through its respective cell to form a final beam; and
measuring the fringe pattern of the final beam to determine the refractive index of the blood sample.

8. A method of measuring the glucose level of blood comprising the steps of:
filtering a sample of blood to remove cells and proteins exceeding a predetermined weight;
providing a light source for generating an original beam;
splitting the original beam into first and second beams;
placing a first cell containing the filtered blood sample into the first beam of light;
placing a second cell in the second beam;
recombining the beams of light after each has passed through its respective cell to form a final beam; and
restoring the original fringe pattern using a compensator to determine the refractive index of the blood sample.

9. A device for measuring the glucose level in a blood sample comprising:
a light source for producing a beam of light;
a first mirror for separating the beam of light into a first beam and a second beam;
a first cell containing a blood sample positioned in said first beam;
a second cell containing a known solution positioned in said second beam;
a second mirror for recombining said first beam and said second beam into a single light beam; and
a photodetector for detecting the intensity of the recombined beam to determine the refractive index and glucose level of the blood sample.

10. The device of claim 9 including compensator means adjustable to compensate for the difference in path lengths of said first beam and said second beam to make the path length of said second beam the same as the path length of said first beam.

11. The device of claim 9 wherein said light source is a white light source.

* * * * *